(12) United States Patent
Matsuura (10) Patent No.: US 10,213,534 B2
(45) Date of Patent: Feb. 26, 2019

(54) BLOOD PROCESSING FILTER AND BLOOD PROCESSING FILTER MANUFACTURING METHOD

(71) Applicant: ASAHI KASEI MEDICAL CO., LTD., Tokyo (JP)

(72) Inventor: Yoshimasa Matsuura, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 92 days.

(21) Appl. No.: 15/026,478

(22) PCT Filed: Oct. 2, 2014

(86) PCT No.: PCT/JP2014/076428
§ 371 (c)(1),
(2) Date: Mar. 31, 2016

(87) PCT Pub. No.: WO2015/050215
PCT Pub. Date: Apr. 9, 2015

(65) Prior Publication Data
US 2016/0243293 A1    Aug. 25, 2016

(30) Foreign Application Priority Data
Oct. 3, 2013    (JP) .................................. 2013-208406

(51) Int. Cl.
*A61M 1/34*    (2006.01)
*A61M 1/02*    (2006.01)
(Continued)

(52) U.S. Cl.
CPC ............ *A61M 1/0281* (2013.01); *A61M 1/34* (2013.01); *A61M 1/341* (2014.02);
(Continued)

(58) Field of Classification Search
None
See application file for complete search history.

(56) References Cited

U.S. PATENT DOCUMENTS

| 4,157,967 A | * | 6/1979 | Meyst | ................... A61M 5/165 |
| | | | | 210/449 |
| 4,170,056 A | | 10/1979 | Meyst et al. | |

(Continued)

FOREIGN PATENT DOCUMENTS

| CN | 101282750 | 10/2008 |
| CN | 101646469 | 2/2010 |

(Continued)

OTHER PUBLICATIONS

Search Report issued in counterpart Patent Application No. EP14850719.7, dated Sep. 9, 2016.

(Continued)

*Primary Examiner* — Chester T Barry
(74) *Attorney, Agent, or Firm* — Greenblum & Bernstein, P.L.C.

(57) ABSTRACT

A blood processing filter for removing undesirable components from liquid containing a blood component or blood, comprises: a sheet-shaped filter element; and a container that includes an inlet-side container element and an outlet-side container element that are disposed to clamp the filter element, and has an internal space separated by the filter element into an inlet space and an outlet space, wherein the filter element includes a filtering surface on a side of the inlet space, a filtering surface on a side of the outlet space, and an end surface along peripheries of the pair of filtering surfaces, and the inlet-side container element and the outlet-side container element are provided with a gripper, and the (Continued)

gripper clamps and compresses an outer edge portion of the pair of filtering surfaces, and is caused to adhere to the end surface with melt resin.

10 Claims, 9 Drawing Sheets

(51) Int. Cl.
    *A61M 1/36* (2006.01)
    *B29C 45/14* (2006.01)
    *B29K 69/00* (2006.01)
    *B29L 31/14* (2006.01)

(52) U.S. Cl.
    CPC ............ *A61M 1/3496* (2013.01); *A61M 1/36* (2013.01); *A61M 1/3635* (2014.02); *A61M 1/3636* (2014.02); *A61M 2202/0439* (2013.01); *A61M 2205/3334* (2013.01); *A61M 2205/7545* (2013.01); *A61M 2207/00* (2013.01); *B29C 45/14467* (2013.01); *B29K 2069/00* (2013.01); *B29L 2031/14* (2013.01)

(56) References Cited

U.S. PATENT DOCUMENTS

| | | | |
|---|---|---|---|
| 5,688,460 A | 11/1997 | Ruschke | |
| 5,723,047 A * | 3/1998 | Turnbull | B01D 29/012 210/445 |
| 5,772,831 A | 6/1998 | Moro et al. | |
| 5,802,643 A * | 9/1998 | Sloot | A47C 7/386 297/220 |
| 6,032,807 A | 3/2000 | Sternberg et al. | |
| 6,143,174 A | 11/2000 | Graus | |
| 6,733,771 B1 * | 5/2004 | Minard | A01K 5/015 424/400 |
| 7,534,348 B2 * | 5/2009 | Reitz | A61M 1/3633 210/232 |
| 2005/0010192 A1 * | 1/2005 | Sun | A61K 8/19 604/501 |
| 2005/0056580 A1 | 3/2005 | Reitz et al. | |
| 2006/0049097 A1 | 3/2006 | Cavallini et al. | |
| 2006/0108272 A1 | 5/2006 | Ariagno et al. | |
| 2009/0045131 A1 | 2/2009 | Omori et al. | |
| 2010/0084326 A1 | 4/2010 | Takesawa | |
| 2012/0067811 A1 | 3/2012 | Yokomizo et al. | |
| 2012/0165176 A1 | 6/2012 | Andou | |

FOREIGN PATENT DOCUMENTS

| | | |
|---|---|---|
| CN | 202554574 | 11/2012 |
| EP | 0526678 | 2/1993 |
| GB | 2266477 | 11/1993 |
| JP | 52-116969 | 9/1977 |
| JP | 6-79110 | 3/1994 |
| JP | 7-267871 | 10/1995 |
| JP | 9-168703 | 6/1997 |
| JP | 11-216179 | 8/1999 |
| JP | 2000-517240 | 12/2000 |
| JP | 4891080 | 3/2012 |
| JP | 2012-192749 | 10/2012 |
| WO | 95/17236 | 6/1995 |
| WO | 2004/050147 | 6/2004 |
| WO | 2012/039402 | 3/2012 |

OTHER PUBLICATIONS

Search Report issued in PCT/JP2014/076428 Patent Application No., dated Nov. 11, 2014.
International Preliminary Report of Patentability issued in Patent Application No. PCT/JP2014/076428, dated Apr. 14, 2016.

* cited by examiner

BLOOD PROCESSING FILTER AND BLOOD PROCESSING FILTER MANUFACTURING METHOD

TECHNICAL FIELD

The present invention relates to a blood processing filter for removing undesirable components, such as aggregates and leukocytes, from liquid containing blood components or blood, and to a blood processing filter manufacturing method. In particular, the present invention relates to a disposable blood processing filter for removing microaggregates and leukocytes which may cause side effects from whole blood preparations, erythrocyte preparations, thrombocyte preparations, blood plasma preparations and the like for blood transfusion, as well as a method for manufacturing the blood processing filter.

BACKGROUND ART

It is becoming common for whole blood collected from a donor to be separated into blood component preparations, such as an erythrocyte preparation, a thrombocyte preparation, and a blood plasma preparation, stored and then provided for transfusion. Since microaggregates and leukocytes included in these blood preparations cause various side effects during blood transfusion, many methods of removing these undesirable components before blood transfusion and then performing transfusion, or performing transfusion with preparations with undesirable components having been removed after blood collection and then temporarily been stored, have been widely used.

Among methods of removing these undesirable components from blood preparations, treatment of blood preparations through a blood processing filter is most typical. As blood processing filters, filter elements with an outer edge portion that are made of nonwoven fabric, porous body or the like being internally mounted in containers by heating bonding, such as heat seal, high frequency bonding, or ultrasonic bonding have been known (e.g., Patent Literatures 1 to 5). In the heating bonded blood processing filter, the outer edge portion of the filter element is melted and integrated with the container, thereby preventing side leakage (side flow) of blood from flowing over the outer edge portion of the filter element without being filtered.

Furthermore, as another blood processing filter, what includes an inlet-side hard container element and an outlet-side hard container element which are joined with each other, and rib-shaped convexes provided for the inlet-side hard container element and the outlet-side hard container element are pressed against each other to thereby clamp the outer edge portion of the filter element has been known. In the blood processing filter using the convexes, the convexes are compressed to each other to a high density, thereby preventing side leakage (side flow) of blood. If such a type of blood processing filter is manufactured using a flexible container element, occurrence of the side flow cannot be reduced to a practical use level.

CITATION LIST

Patent Literature

[Patent Literature 1] Japanese Unexamined Patent Publication No. H11-216179
[Patent Literature 2] Japanese Unexamined Patent Publication No. H7-267871
[Patent Literature 3] International Publication No. 2004/050147
[Patent Literature 4] International Publication No. 95/17236
[Patent Literature 5] European Unexamined Patent Publication No. 0526678

SUMMARY OF INVENTION

Technical Problem

However, according to the heating bonded blood processing filter as shown in Patent Literatures 1 to 5, a melted portion and its outer portion of front and back filtering surfaces of a filter element do not function as filtering surfaces. Consequently, it is difficult to improve the blood treatment efficiency. According to a blood processing filter using convexes, if a compression region due to the convex is small, blood is facilitated to flow over an outer edge portion of the filter element. Consequently, in order to securely remove undesirable components, for example, a scheme for increasing the compression region at penalty in effective filtering area and the like are required, and it is also difficult to facilitate improvement in blood treatment efficiency.

The present invention has an object to solve such a problem, and to provide a blood processing filter that has no risk of incomplete removal of undesirable components and can improve the blood treatment efficiency, and to provide a blood processing filter manufacturing method.

Solution to Problem

The present inventors have diligently researched to solve the problems, and resultantly found that not only the outer edge portion of the filtering surfaces on the front and back of the filter element are clamped by a gripper but also the end surface along the peripheries of the filtering surfaces is bonded to the gripper with melt resin, thereby facilitating widening the effective filtering area, and improving the blood treatment efficiency, and reached the present invention.

That is, an aspect of the present invention is a blood processing filter for removing undesirable components from liquid containing a blood component or blood, comprising: a sheet-shaped filter element; and a container that includes an inlet-side container element and an outlet-side container element that are disposed to clamp the filter element, and has an internal space separated by the filter element into an inlet space and an outlet space, wherein the filter element includes a filtering surface on a side of the inlet space, a filtering surface on a side of the outlet space, and an end surface along peripheries of the pair of filtering surfaces, and the inlet-side container element and the outlet-side container element are provided with a gripper, and the gripper clamps and compresses the outer edge portion of the pair of filtering surfaces, and is caused to adhere to the end surface with melt resin.

The blood processing filter can prevent a side leakage (side flow) where undesirable components flow over the outer edge portion of the filter element without being filtered, by the gripper that clamps and compresses the outer edge portion of the filter element at the pair of filtering surfaces. Furthermore, since the gripper is caused to adhere to the end surface of the filter element with the melt resin, the area of the outer edge portion that is compressed by the gripper can be facilitated to be reduced, which is advantageous to improve the blood treatment efficiency.

It is further preferred that in the blood processing filter, the filter element be not melted at the gripper. Thus, it is further advantageous to improve the blood treatment efficiency.

It is further preferred that in the blood processing filter, the same material as that of the container be adopted for the melt resin. Thus, adhesion between the filter element and the container is facilitated.

Furthermore, the inlet-side container element and the outlet-side container element may be made of a flexible resin. The inlet-side container element and the outlet-side container element that are made of the flexible resin are adopted to constitute the flexible container, thereby allowing the present invention to enjoy the advantages in comparison with the case of the hard container.

It is preferred that the gripper of the blood processing filter further include a resin flow path that surround the end surface of the filter element and be provided with the melt resin. Thus, the filter element is installed in the container and the resin flow path is filled with the melt resin, thereby allowing the end surface of the filter element to adhere to the gripper at the portion of the resin flow path.

It is further preferred that in the blood processing filter, the inlet-side container element, the outlet-side container element, and the filter element adhere over the entire periphery of the gripper in a belt-shaped manner by the resin flow path being filled with the melt resin. Thus, the airtightness and liquid-tightness are increased.

A method of manufacturing a blood processing filter according to an aspect of the present invention is a method of manufacturing a blood processing filter for removing undesirable components from liquid containing a blood component or blood, the method comprising: an injection molding step of injection-molding an inlet-side container element using one mold, and an outlet-side container element using another mold; a inserting step of inserting a filter element into the inlet-side container element or the outlet-side container element; a joining step of mold-fitting the molds, and joining the inlet-side container element and the outlet-side container element to each other; and an adhesion step of causing the inlet-side container element and the outlet-side container element to adhere to each other with melt resin, wherein the filter element includes a filtering surface on a side of an inlet space, a filtering surface on a side of an outlet space, and an end surface along peripheries of the pair of filtering surfaces, and the inlet-side container element and the outlet-side container element are provided with a gripper, and the gripper clamps and compresses an outer edge portion of the pair of filtering surfaces, and is caused to adhere to the end surface with melt resin.

According to this, the joining step of mold-fitting the molds and joining the inlet-side container element and the outlet-side container element, thereby allowing the inlet-side container element and the outlet-side container element to be pressed against each other by a strong force. Consequently, the outer edge portion of the filtering surfaces and of the filter element can be compressed to have high density by the gripper, which is advantageous to prevent a side leakage (side flow) where undesirable components flow over the outer edge portion of the filter element without being filtered. Furthermore, since the gripper is caused to adhere to the end surface of the filter element with the melt resin, the area of the outer edge portion that is compressed by the gripper can be facilitated to be reduced, which is advantageous to improve the blood treatment efficiency.

Advantageous Effects of Invention

The blood processing filter and the blood processing filter manufacturing method according to the present invention can negate the risk of incomplete removal of undesirable components, and facilitate improvement of the blood treatment efficiency.

DESCRIPTION OF EMBODIMENT

Hereinafter, referring to the drawings, preferred embodiments of a blood processing filter according to the present invention are described in detail.

Figure 1:
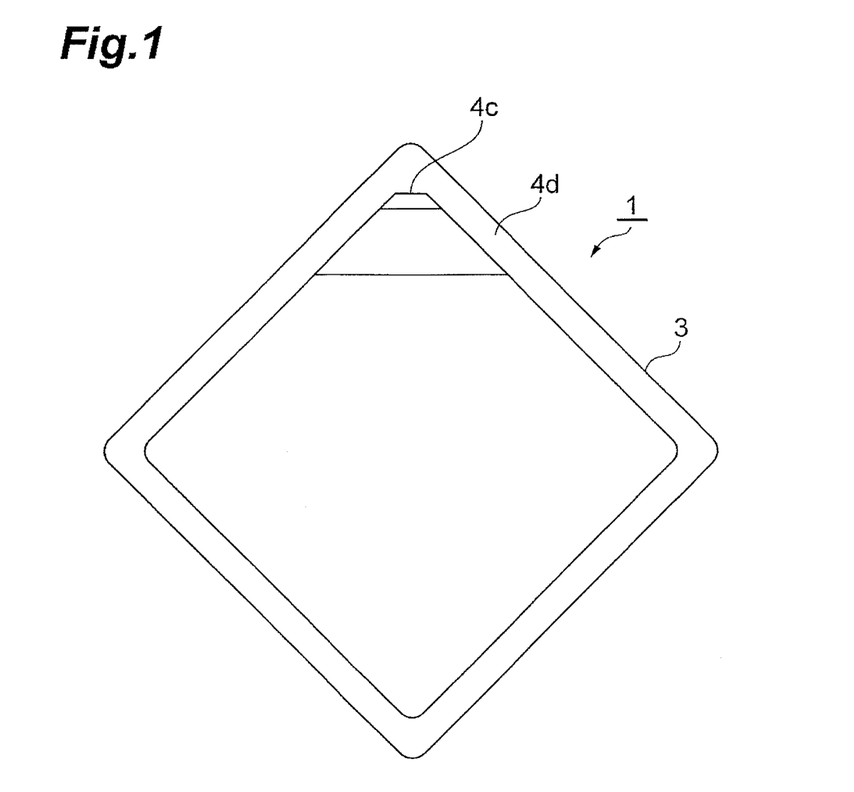
FIG. 1 is a top view of a blood processing filter according to an embodiment of the present invention.
Figure 2:
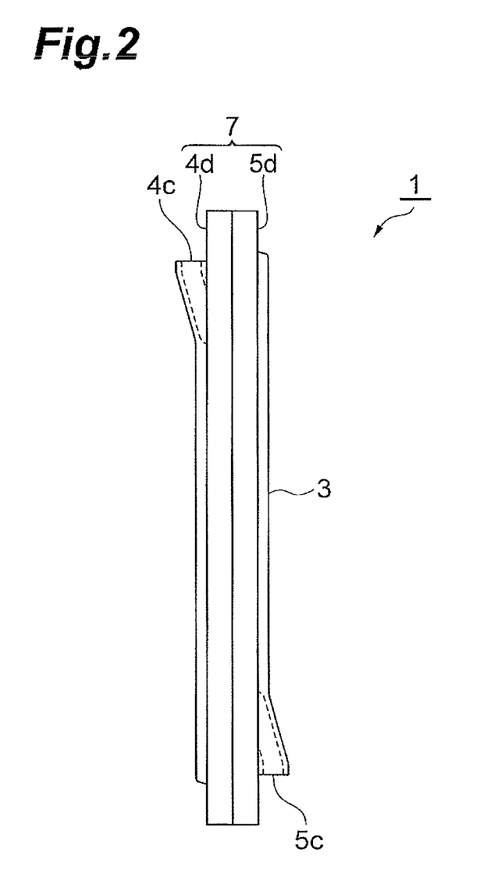
FIG. 2 is a side view of the blood processing filter according to the embodiment of the present invention.
Figure 3:
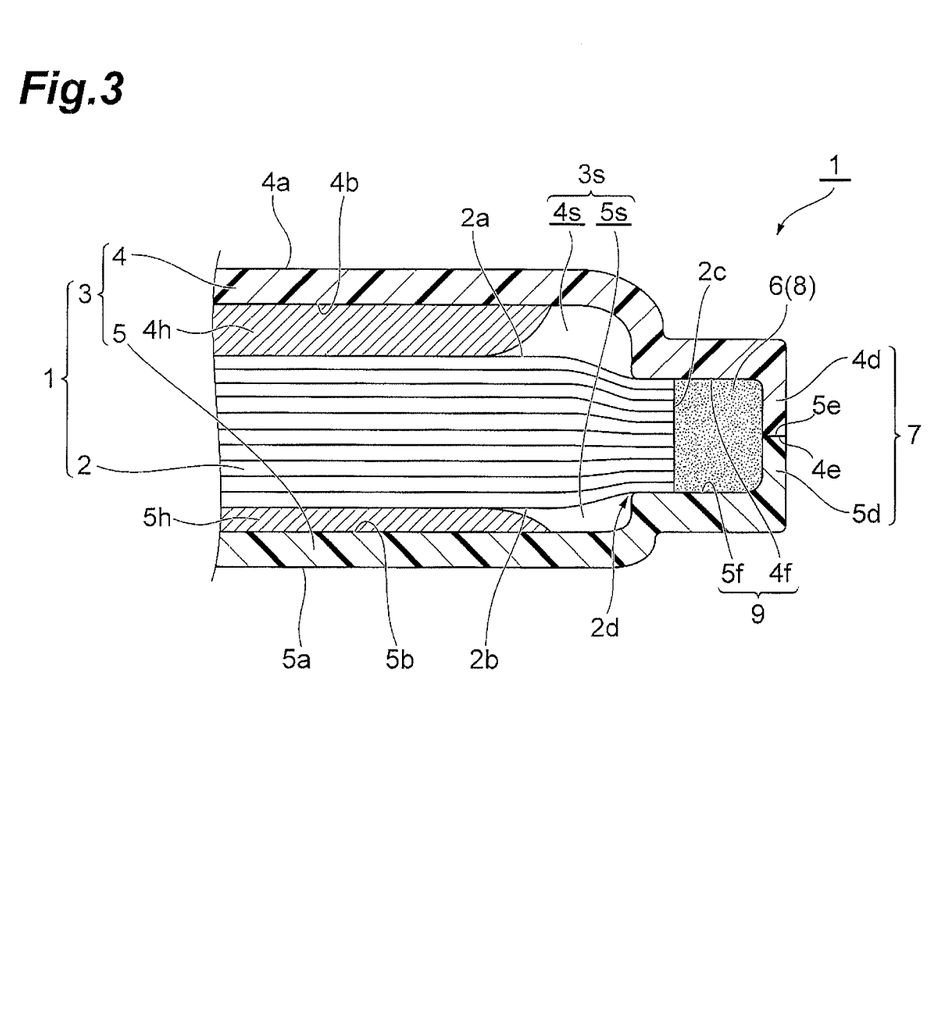
FIG. 3 is an enlarged sectional view of a gripper.

First, referring to FIGS. 1 to 3, a blood processing filter 1 relating to an embodiment of the present invention is described. The blood processing filter 1 is for removing undesirable components from liquid containing blood components or blood (hereinafter, referred to as liquid to be treated). The blood processing filter 1 has a square shape as a whole, and includes a sheet-shaped filter element 2 and a container 3. The container 3 includes an inlet-side container element 4 and an outlet-side container element 5 that are disposed to clamp the filter element 2. An internal space 3s is separated by the filter element 2 into an inlet space 4s and an outlet space 5s. Although the blood processing filter 1 may have any of a rectangular shape, a disk shape, elliptic shape and the like, the rectangular shape is preferable to reduce the loss of material during manufacturing. A square, a rectangle, and a rhombus are regarded as types of rectangular shapes.

The filter element 2 is a square filter member that has a filtering surface 2a on the inlet space 4s side and a filtering surface 2b on the outlet space 5s side, and an end surface 2c along the peripheries of the pair of filtering surfaces 2a and 2b. The filter element 2 may be made of a well-known filtering medium, such as a fibrous and porous medium, e.g., nonwoven fabric, woven fabric or the like, or a porous body having three-dimensional continuous reticulate pores, e.g., spongiform fabric. What is not excellent at adhesion, such as mesh or a screen, is preferable. Examples of the materials of the filter element 2 include polypropylene, polyethylene, styrene-isobutylene-styrene copolymer, polyurethane, polyester and the like. The case where the filter element 2 is made of nonwoven fabric is preferable particularly in view of productivity.

The filter element 2 may be a single filter element, or made of a plurality of filter elements. In the case where the element is made of a plurality of filter elements, it is preferred to include a first filter element that is disposed upstream and mainly removes microaggregates, and a second filter element that is disposed downstream of the first filter element for removing undesirable components other than microaggregates. For example, a filter material made of nonwoven fabric having fiber diameters ranging from several to several tens of micrometers is disposed on the inlet side as the first filter element for mainly removing aggregates, a filter material made of nonwoven fabric having fiber diameters ranging from 0.3 to 3.0 µm is disposed as the second filter element for removing other undesirable components, and a post filter having a specific space on a further downstream side is stacked and used. Each of the first and second filter materials may be made of a plurality of types of filter materials. Alternatively, only one of these materials may be made of multiple filter materials. For example, a first filter material made of at least one of nonwoven fabric having fiber diameters ranging from 30 to 40 µm and nonwoven fabric having fiber diameters ranging from 10 to 20 µm may be disposed on the upstream side, and a second filter material made of at least one of nonwoven fabric having fiber diameters ranging from 1.5 to 2.5 µm and nonwoven fabric having fiber diameters ranging from 0.5 to 1.8 µm may be disposed on the downstream side of the first filter material, and these materials may be used. Alternatively, nonwoven fabric having large fiber diameters and nonwoven fabric having small fiber diameters may be alternately arranged. It is however preferred that the nonwoven fabric having large fiber diameters be arranged on the upstream side.

The container 3 is a square container having a predetermined thickness, and includes the inlet-side container element 4 and the outlet-side container element 5 which are arranged to clamp the filter element 2. The internal space 3s of the container 3 is separated by the filter element 2 into the inlet space 4s and the outlet space 5s.

The inlet-side container element 4 is a square member that is a cut of the container 3 having substantially half the thickness, and includes an outer surface 4a, an inner surface 4b, and an end surface 4e along the peripheries of the outer surface 4a and the inner surface 4b. An inlet 4c is provided at one corner of the outer surface 4a (see FIG. 1). Meanwhile, the outlet-side container element 5 is a square member that is the rest of the container 3, and includes an outer surface 5a, an inner surface 5b, and an end surface 5e along the peripheries of the outer surface 5a and the inner surface 5b. An outlet 5c is provided at the corner of the outer surface 5a opposite to the corner provided with the inlet 4c (see FIG. 2). The inlet 4c and the outlet 5c are provided such that the inlet 4c opens upward and the outlet 5c opens downward during use of the blood processing filter 1.

An outer edge portion including the end surfaces 4e and 5e of the inlet-side container element 4 and the outlet-side container element 5 is provided with an inlet-side contact portion 4d and an outlet-side contact portion 5d, respectively, which are brought into contact with each other to constitute a contact portion 7. The inlet-side contact portion 4d and the outlet-side contact portion 5d have a shape where external peripheral walls with the end surfaces 4e and 5e fanned thereon are made vertical so as to cause the end surfaces 4e and 5e to face each other. In this embodiment, the end surfaces 4e and 5e are flat surfaces but may have female and male relationship to be fitted with each other.

The inlet-side container element 4 and the outlet-side container element 5 are provided with an inlet-side gripper 4f and an outlet-side gripper 5f that hold the outer edge portion 2d of the filter element 2 including the end surface 2c, at the inner edges of the inlet-side contact portion 4d and the outlet-side contact portion 5d, respectively. The inlet-side gripper 4f is made of a step of swelling of the inlet-side container element 4 on the inner surface 4b side. Likewise, the outlet-side gripper 5f is made of a step of swelling of the outlet-side container element 5 on the inner surface 5b side. The inlet-side gripper 4f and the outlet-side gripper 5f clamp and compress the outer edge portion 2d of the pair of filtering surfaces 2a and 2b of the filter element 2.

The gripper 9, which comprises the inlet-side gripper 4f and the outlet-side gripper 5f, has a predetermined width at the outer edge portion of the container 3, and the inner portion thereof is used to hold the filter element 2. The outer portion thereof serves as a resin flow path 8 that surrounds the end surface 2c of the filter element 2 and is provided with the melt resin 6. The resin flow path 8 is a tubular cavity formed of the outer portion of the inlet-side gripper 4f, the outer portion of the outlet-side gripper 5f, the inlet-side contact portion 4d, the outlet-side contact portion 5d, and the end surface 2c of the filter element 2. The resin flow path 8 has a through-hole (not shown) that communicates with the outside of the container 3. The number of through-holes may be one or more. The resin flow path 8 is filled with the melt resin 6 through the through-hole, thereby causing the gripper 9 to adhere to the end surface 2c with the melt resin 6. This causes the filter element 2 to adhere to the inlet-side container element 4 and the outlet-side container element 5 on the end surface 2c at the gripper 9 with the melt resin 6. With such a belt-shaped adhesion of the inlet-side container element 4, the outlet-side container element 5, and the filter element 2 along the entire periphery of the gripper 9, the container 3 is sealed, which improves the airtightness and liquid-tightness.

The filter element 2 is not melted at the gripper 9. This is because the method of adhesion between the filter element 2 and the container 3 is not based on heating bonding, such as ultrasonic bonding. According to the heating bonding, the filter element 2 is melted and causes a portion integrated with the material of the container 3. The filter element 2 maintains the function as a filter at areas other than the end surface 2c adhering to the gripper 9 with the melt resin 6. This is because the method of adhesion between the filter element 2 and the container 3 is not based on the heating bonding, such as ultrasonic bonding, and the filter element 2 is sufficiently compressed at the gripper 9 and the melt resin 6 injected into the resin flow path 8 does not enter the inside of the end surface 2c of the filter element 2. If the melt resin 6 enters the inside of the filter element 2 from the end surface 2c, the portion cannot maintain the function as the filter.

A plurality of convex ribs 4h and 5h are provided on further inner sides of the inlet-side gripper 4f and the outlet-side gripper 5f on the inner surface 4b side of the inlet-side container element 4 and the inner surface 5b side of the outlet-side container element 5. The rib 4h is pressed against the filtering surface 2a of the filter element 2, and secures the inlet space 4s between the filtering surface 2a and the inner surface 4b of the inlet-side container element 4. Likewise, the rib 5h is pressed against the filtering surface 2b of the filter element 2, and secures the outlet space 5s between the filtering surface 2b and the inner surface 5b of the outlet-side container element 5. Thus, the filter element 2 is in a state where the pair of filtering surfaces 2a and 2b are clamped by the ribs 4h and 5h and compressed. The rib 4h is higher than the rib 5h, and the inlet space 4s is secured wider than the outlet space 5s. The heights of the ribs 4h and 5h may be the same. Alternatively, the rib 5h may be higher than the rib 4h.

The material of the container 3 and the melt resin 6 may be flexible material or hard material, for example, polycarbonate, polyester, polyamide, polystyrene, ABS, polyethylene, polypropylene, polyvinyl chloride, SBS, thermoplastic elastomer such as styrene-butadiene block copolymer, partially hydrogenated thermoplastic elastomer such as SBS, all types of thermoplastic resin such as perfectly hydrogenated styrene elastomer, thermosetting resin or the like. The materials used for the container 3 and the melt resin 6 may be the same or different; it is sufficient that materials that can easily adhere to each other are selected. For example, polystyrene resin, thermoplastic elastomer such as SBS, partially hydrogenated thermoplastic elastomer such as SBS, perfectly hydrogenated styrene elastomer, or resin with a high water vapor permeability such as flexible polyvinyl chloride is used as the material of the container 3, thereby allowing even the inside of the blood processing filter 1 to be sterilized by autoclave sterilization performed after the blood processing filter 1 is connected to the blood circuit. As to the material of the melt resin 6, since a resin with a lower melt viscosity is more conformable with the resin of the filter element 2, the adhesive strength between the end surface 2c of the filter element 2 and the melt resin 6 can be improved.

In the case of insertion in a centrifuge together with the blood bag during blood component separation, a flexible container is more preferable than a hard container. In this case, for example, polyvinyl chloride, SBS, thermoplastic elastomer such as styrene-butadiene block copolymer, partially hydrogenated thermoplastic elastomer such as SBS, perfectly hydrogenated styrene elastomer or other resin can be used as the material of the flexible container, and it is preferred that the Young's modulus be 1 GPa or lower. In the blood processing filter 1 according to this embodiment, the inlet-side container element 4 and the outlet-side container element 5 are formed of a flexible resin to thereby be a container having flexibility (flexible container) 3. As a result, various advantages in the case of using the flexible container can be enjoyed, which is excellent.

Figure 4:
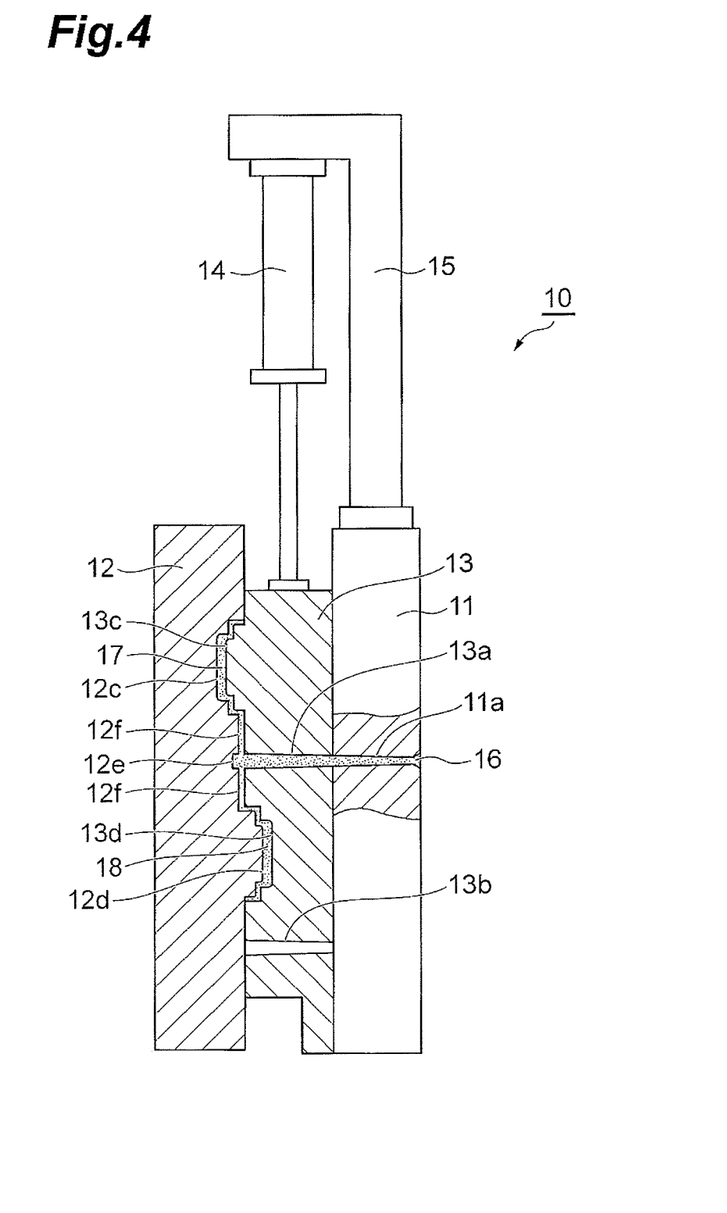
FIG. 4 is an illustration diagram for illustrating an injection molding step in manufacturing the blood processing filter according to the embodiment.

Next, an example of a method for manufacturing the blood processing filter 1 is described. As shown in FIG. 4, the injection molding machine 10 includes a fixed die 11, a movable die 12, and a slidable die 13. The fixed die 11 is fixed to fixed platen (not shown) of the injection molding machine 10. A platform 15 that includes a cylinder 14 for sliding is provided on the upper surface of the fixed die 11. The cylinder 14 that is hydraulically or pneumatically moved is coupled onto the upper surface of the slidable die 13. The slidable die 13 is configured so as to be slidable and movable in a vertical direction while the state of being in close contact with a side surface of the fixed die 11 is kept.

The movable die 12 is attached to a movable platen (not shown) that is horizontally movable with respect to the injection molding machine 10. The movable platen is configured to be movable in a manner of approaching and being apart from the fixed die 11 by a mold opening and closing device (not shown) of the injection molding machine 10. The movable die 12 is configured to be movable between a mold fitting position of being in close contact with the slidable die 13, and a mold opening position of being apart from the slidable die 13.

The fixed die 11 is provided, at its center, with a sprue 11a for guiding melt resin 16 injected from an injector (not shown) attached to the fixed die 11. The slidable die 13 is provided with a central sub-sprue 13a that continuously communicates with the sprue 11a when the die is at a lower position, and with a lower sub-sprue 13b that continuously communicates with the sprue 11a when the die is at an upper position.

Figure 5:
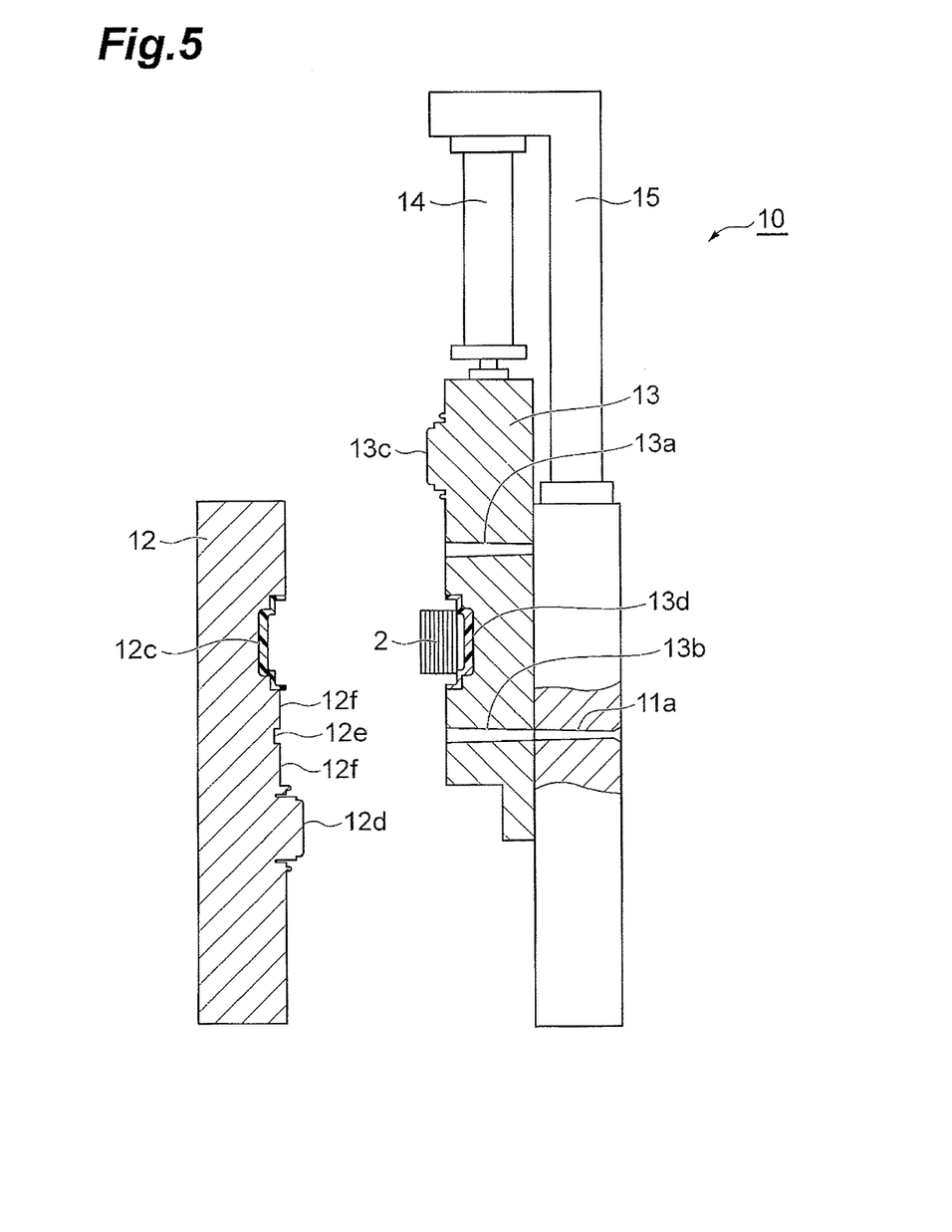
FIG. 5 is an illustration diagram for illustrating a inserting step in manufacturing the blood processing filter according to the embodiment.
Figure 6:
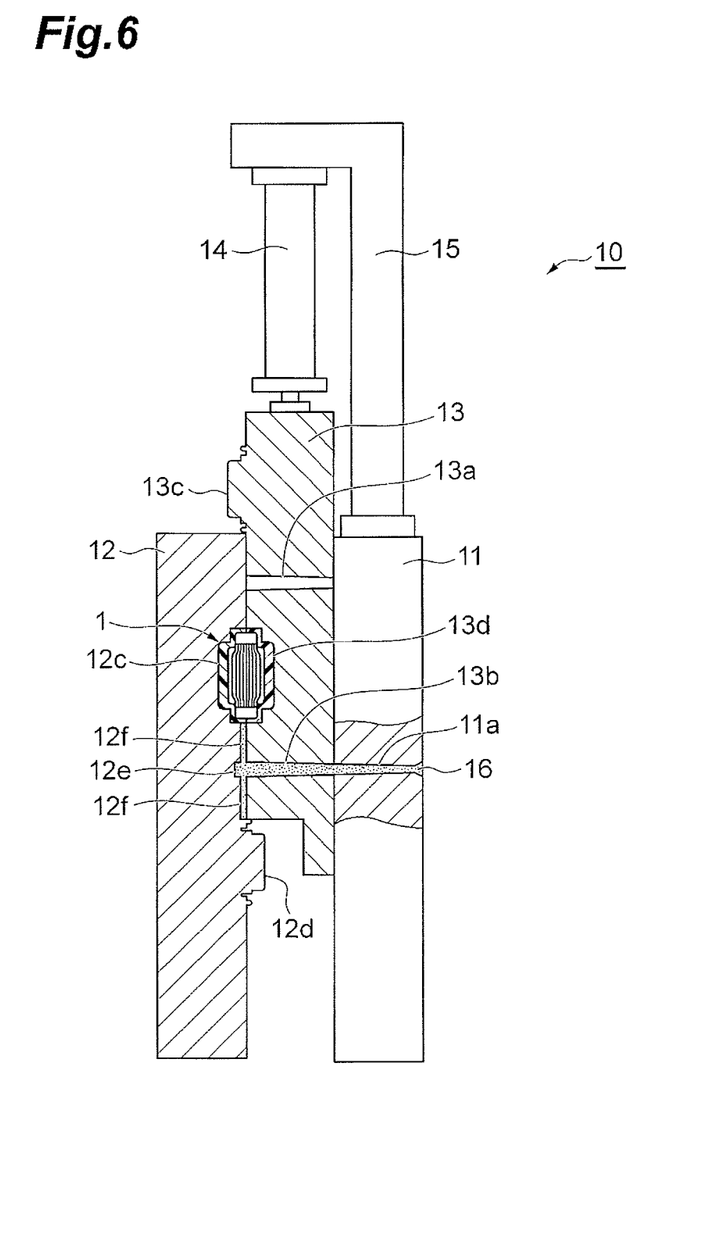
FIG. 6 is an illustration diagram for illustrating a joining step in manufacturing the blood processing filter according to the embodiment of the present invention.

A mold fitting surface of the slidable die 13 is provided with a male mold 13c and a female mold 13d at vertically symmetric positions with respect to the central sub-sprue 12a. The male mold 13c is for molding the inner surface 4b of the inlet-side container element 4, and the female mold 13d is for molding the outer surface 5a of the outlet-side container element 5. On the other hand, a mold fitting surface of the movable die 12 is provided with a female mold 12c and a male mold 12d facing the respective male mold 13c and female mold 13d when the slidable die 13 is at the lower position. The female mold 12c is for molding the outer surface 4a of the inlet-side container element 4, and the male mold 12d is for molding the inner surface 5b of the outlet-side container element 5. As shown in FIGS. 5 and 6, the female mold 12c on the movable die 12 side is configured to face the female mold 13d on the slidable die 13 side when the slidable die 13 is at the upper position.

As shown in FIG. 4, when the slidable die 13 is at the lower position and the movable die 12 is mold-fitted therewith, a pair of gaps 17 and 18 surrounded respectively by the male molds 12d and 13c and the female molds 13d and 12c are formed between the slidable die 13 and the movable die 12. At this time, the central sub-sprue 13a of the slidable die 13 is configured to communicate with these gaps through a runner 12e formed from the edge portions of the female molds 13d and 12c at the movable die 12 and through a pair of gates 12f. As shown in FIG. 6, when the slidable die 13 is at the upper position and the movable die 12 is mold-fitted therewith, the female molds 13d and 12c of the slidable die 13 and the movable die 12 fit with each other, and the lower sub-sprue 13b and the runner 12e communicate with the edge portions of these female molds 13d and 12c through the gates 12f.

In order to mold the blood processing filter 1 using such an injection molding machine 10, first, as shown in FIG. 4, the cylinder 14 is elongated to place the slidable die 13 at the lower position. Then, the movable platen of the injection molding machine 10 is moved on the fixed platen side, and mold-fits the slidable die 13 and the movable die 12. In this state, as shown in FIG. 4, the central sub-sprue 13a of the slidable die 13 communicates with the sprue 11a of the fixed die 11, and the pair of gaps 17 and 18 is formed between the slidable die 13 and the movable die 12. Next, the melt resin 16 is injected from the injector attached to the fixed platen, and the melt resin 16 is guided to both the gaps 17 and 18 through the sprue 11a of the fixed die 11, the central sub-sprue 13a of the slidable die 13, the runner 12e, and the gates 12f, and these gaps 17 and 18 are filled therewith. Thus, the inlet-side container element 4 and outlet-side container element 5 are formed in the respective gaps 17 and 18 (injection molding step).

After the inlet-side container element 4 and outlet-side container element 5 are cooled and solidified, the movable die 12 and the slidable die 13 are mold-opened by the mold opening and closing device and separated as shown in FIG. 5. Then, the male molds 13c and 12d are separated from the inlet-side container element 4 and the outlet-side container element 5, and the inlet-side container element 4 and the outlet-side container element 5 are left on the female molds 12c and 13s. In the mold opening, the resin portions solidified in the sprue 11a, the sub-sprue 13a, the runner 12e, the gates 12f and the like of the molds are pushed out of and dropped from the molds. An outer edge portion including the end surfaces 4e and 5e of the thus obtained inlet-side container element 4 and outlet-side container element 5 is formed with an inlet-side contact portion 4d and an outlet-side contact portion 5d which are brought into contact with each other to constitute a contact portion 7.

Next, the filter element 2 made of polyester nonwoven fabric is inserted into the outlet-side container element 5, and subsequently the cylinder 14 is retracted to move the slidable die 13 to the upper position (inserting step). Then, the female mold 13d of the slidable die 13 and the female mold 12c of the movable die 12 face with each other, the inlet-side container element 4 and the outlet-side container element 5 left on the female molds 13d and 12c are brought into a state of facing each other. At this time, the lower sub-sprue 13b of the slidable die 13 is placed so as to communicate with the sprue 11a of the fixed die 11. In this embodiment, the example where the filter element 2 is inserted in the outlet-side container element 5 is described. Alternatively, an exemplary example where the filter element 2 is inserted in the inlet-side container element 4 may be adopted.

In this state, the movable die 12 is moved toward the slidable die 13, and these dies are brought into contact and mold-fitted with each other as shown in FIG. 6, thereby joining the inlet-side container element 4 and the outlet-side container element 5 with each other (joining step). Then, the end surface 4e of the inlet-side contact portion 4d and the end surface 5e of the outlet-side contact portion 5d are fitted with each other to form the contact portion 7. At the inner edge of the contact portion 7, the gripper 9 and the resin flow path 8 are formed. The resin flow path 8 has a through-hole, and communicates with the gate 12f through the through-hole. The gate 12f, in turn, communicates with the sub-sprue 13b through the runner 12e. Consequently, when the melt resin 6 is injected as melt resin 16 from the injector in this state, the melt resin 6 passes through the sprue 11a of the fixed die 11, the sub-sprue 13b, the runner 12e, the gate 12f and the through-hole, and the resin flow path 8 is filled with the resin. Thus, the inlet-side container element 4 and the outlet-side container element 5 are caused to adhere to each other at the periphery of the gripper 9 with the melt resin 6 (adhesion step). As described above, according to the method of filling with the melt resin 6 after formation of the resin flow path 8, control of the amount of resin is facilitated.

Figure 7:
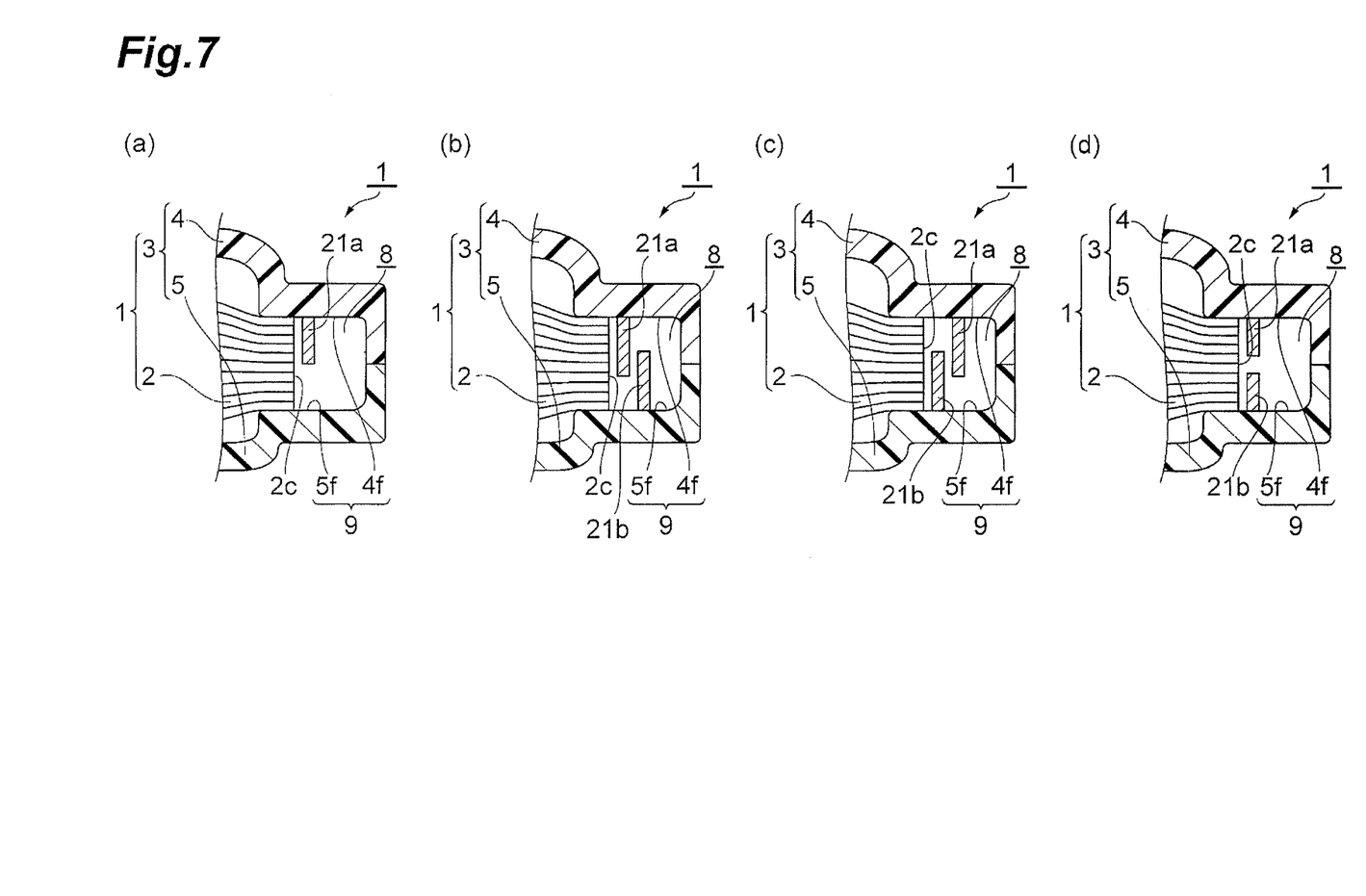
FIG. 7 is an enlarged sectional view of a gripper provided with baffle plates.

Adjusting of the position provided with the through-hole in the case of injection of the melt resin 6 into the resin flow path 8 may allow the melt resin 6 to be injected in the direction perpendicular to the end surface 2c of the filter element 2, or allow the melt resin 6 to be injected in the direction parallel to the end surface 2c. Preferably, to reduce the deformation of the filter element 2, it is desired that the pressure of injection not be applied to the filter element 2. Thus, a baffle plate structure or the like can be arranged. For example, as shown in FIG. 7(a), a baffle plate 21a is provided nearer to the end surface 2c side than the through-hole (not shown) of the resin flow path 8, at the inlet-side gripper 4f, in parallel to the end surface 2c of the filter element 2. The length of the baffle plate 21 is smaller than the thickness of the end surface 2c of the filter element 2 (the length of the compression direction). For example, as shown in FIG. 7(b), a baffle plate 21b may be provided also at the outlet-side gripper 5f in parallel to the end surface 2c of the filter element 2 so as to be staggered with the baffle plate 21a. The baffle plates 21a and 21b are provided in an order of the baffle plates 21a and 21b from the end surface 2c. The lengths of the baffle plates 21a and 21b are smaller than the thickness of the end surface 2c of the filter element 2. For example, as shown in FIG. 7(c), baffle plates 21b and 21a may be provided in the order of the baffle plates 21b and 21a from the end surface 2c. For example, as shown in FIG. 7(d), baffle plates 21a and 21b may be provided to have the same distance from the end surface 2c. The lengths of the baffle plates 21a and 21b are smaller than ½ of the thickness of the end surface 2c of the filter element 2. Furthermore, it is preferred that sufficient compression of the filter element 2 by the gripper 9 prevent the melt resin 6 injected into the resin flow path 8 from deforming the filter element 2 or entering the filter element 2. Thus, it is preferred to press the filter element 2 to have the density of that of the original resin. However, any structure can be adopted only if the structure is tolerable against the pressure of the melt resin 6 to be injected.

The slidable die 13 and the movable die 12 are mold-opened again by the mold opening and closing device after the melt resin 6 is cooled and solidified, and the inlet-side container element 4 and the outlet-side container element 5 are caused to adhere to each other, and thus the blood processing filter 1, which is finished as a completely sealed molded product, is obtained. The resin portions solidified in the sprue 11a, the sub-sprue 13b, the runner 12e, the gates 12f and the like are pushed out of and dropped from the molds.

After the thus completed blood processing filter 1 is taken out, the cylinder 14 is elongated again to place the slidable die 13 at the lower position. Then, the movable die 12 and the slidable die 13 are mold-fitted, and transition is made to a molding step for the next product. The series of steps as described above is repeated, thereby allowing the blood processing filters 1 to be successively molded. Furthermore, the molding step includes vertical sliding of the slidable die 13, mold-fitting and mold-opening through forward and backward movement of the movable die 12, and injection of the melt resin 16, which are simple steps. Consequently, all the steps can be easily automated. Therefore, the blood processing filter 1 can be mass-produced.

Thus, only through use of a set of molds 12 and 13 and the injection molding machine 10, processes from injection molding of the inlet-side container element 4 and the outlet-side container element 5, and internal inserting of the filter element 2, and to adhesion of the inlet-side container element 4 and the outlet-side container element 5 can be consecutively performed in a single step, and even what is completely sealed can be molded.

As described above, the blood processing filter 1 includes the sheet-shaped filter element 2, the inlet-side container element 4 and outlet-side container element 5 that are disposed to clamp the filter element 2, and the container 3 whose internal space 2s is separated by the filter element 2 into the inlet space 4s and the outlet space 5s. The filter element 2 has the filtering surface 2a on the inlet space 4s side and the filtering surface 2b on the outlet space 5s side, and the end surface 2c along the peripheries of the pair of filtering surfaces 2a and 2b. The inlet-side container element 4 and the outlet-side container element 5 are provided with the gripper 9. The gripper 9 clamps and compresses the outer edge portion 2d of the pair of filtering surfaces 2a and 2b, and is caused to adhere to the end surface 2c with the melt resin 6.

The blood processing filter 1 comprises the gripper 9 that clamps and compresses the outer edge portion 2d of the pair of filtering surfaces 2a and 2b of the filter element 2, and includes an effective filtering portion on an inner side of the gripper 9. Thus, the side leakage (side flow) where undesirable components flow over the outer edge portion 2d of the filter element 2 without being filtered can be prevented. Furthermore, since the gripper 9 is caused to adhere to the end surface 2c of the filter element 2 with the melt resin 6, the area of the outer edge portion 2d that is compressed by the gripper 9 can be facilitated to be reduced, which increases the area of the effective filtering portion on the inner side of the gripper 9, and is advantageous to improve the blood treatment efficiency.

Furthermore, in the blood processing filter 1, the filter element 2 is not melted at the gripper 9. Consequently, the function as the filter is maintained, which is further advantageous to improve the blood treatment efficiency.

Furthermore, in the blood processing filter 1, the same material as that of the container 3 is used for the melt resin 6. Consequently, adhesion between the filter element 2 and the container 3 is easy.

Furthermore, in the blood processing filter 1, the gripper 9 further includes the resin flow path 8 that surrounds the end surface 2c of the filter element 2 and is provided with the melt resin 6. Thus, the filter element 2 is installed in the container 3 and then the resin flow path 8 is filled with the melt resin 6, thereby allowing the end surface 2c of the filter element 2 to adhere at the portion of the resin flow path 8.

Furthermore, in the blood processing filter 1, the inlet-side container element 4, the outlet-side container element 5, and the filter element 2 adhere over the entire periphery of the gripper 9 in a belt-shaped manner by the resin flow path 8 being filled with the melt resin 6. Consequently, the airtightness and liquid-tightness are high.

The method of manufacturing the blood processing filter 1 comprises: an injection molding step of injection-molding the inlet-side container element 4 with the male mold 13c of the slidable die 13 and the female mold 12c of the movable die 12, and the outlet-side container element 5 with the female mold 13d of the slidable die 13 and the male mold 12d of the movable die 12; a inserting step of inserting the filter element 2 into the inlet-side container element 4 or the outlet-side container element 5; a joining step of mold-fitting the movable die 12 and the slidable die 13 that are a set of molds, and joining the inlet-side container element 4 and the outlet-side container element 5 to each other; and a adhesion step of causing the inlet-side container element 4 and the outlet-side container element 5 to adhere to each other with melt resin 6, wherein the filter element 2 includes the filtering surface 2a on the inlet space 4s side and the filtering surface 2b on the outlet space 5 s side, and the end surface 2c along the peripheries of the pair of the filtering surfaces 2a and 2b, the inlet-side container element 4 and the outlet-side container element 5 are provided with the gripper 9, the gripper 9 clamps and compresses the outer edges 2d of the pair of the filtering surfaces 2a and 2b, and is caused to adhere to the end surface 2c with the melt resin 6.

According to this, the joining step of mold-fitting the movable die 12 and the slidable die 13 with each other and causing the inlet-side container element 4 and the outlet-side container element 5 to adhere to each other, thereby allowing the inlet-side container element 4 and the outlet-side container element 5 to be pressed against each other by a strong force. Consequently, the outer edge portion 2d of the filtering surfaces 2a and 2b of the filter element 2 can be compressed at to have high density by the gripper 9, which is advantageous to prevent a side leakage (side flow) where undesirable components flow over the outer edge portion 2d of the filter element 2 without being filtered. Furthermore, since the gripper 9 is caused to adhere to the end surface 2c of the filter element 2 with the melt resin 6, the area of the outer edge portion 2d that is compressed by the gripper 9 can be facilitated to be reduced, which increases the area of the effective filtering portion on the inner side of the gripper, and is advantageous to improve the blood treatment efficiency.

Figure 8:
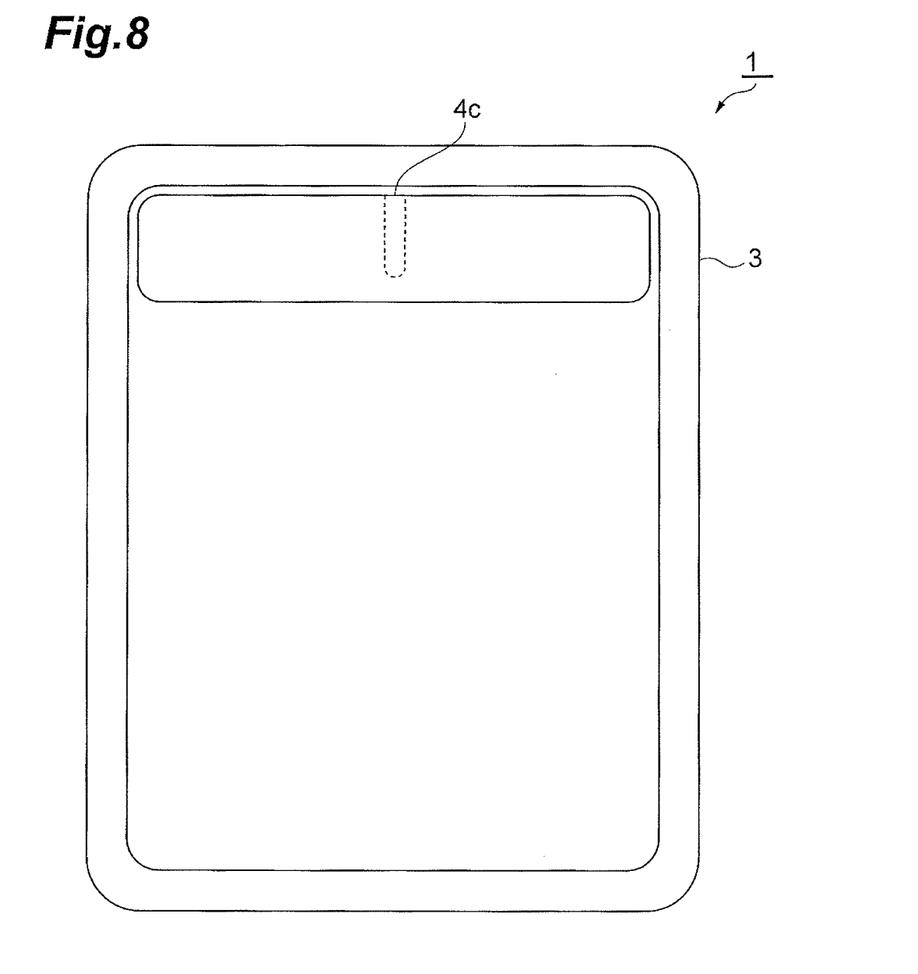
FIG. 8 is a top view of a rectangular blood processing filter.
Figure 9:
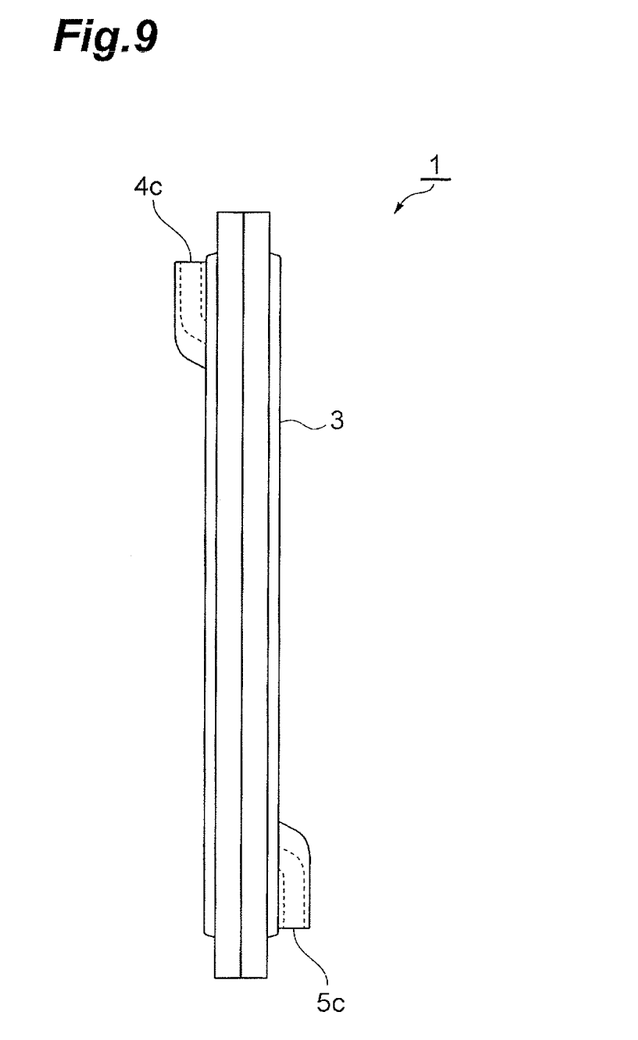
FIG. 9 is a side view of the rectangular blood processing filter.

Although the present invention has thus been described with reference to the embodiments, the present invention is not limited to the embodiments. For example, as shown in FIGS. 8 and 9, the blood processing filter 1 may have a rectangular shape as a whole. The filter element 2 (see FIG. 3) also has a rectangular shape in conformity with the rectangular container 3. The inlet-side container element 4 also has a rectangular shape. The inlet 4c is provided at the central portion on one short side of the inlet-side container element 4 so as to open on one side. The outlet-side container element 5 also has a rectangular shape. The outlet 5c is provided at the central portion on the other short side of the outlet-side container element 5 so as to open on the other side. For example, the inlet-side container element 4 and the outlet-side container element 5 may be joined to each other by heating bonding, such as ultrasonic bonding. That is, after the inlet-side contact portion 4d and the outlet-side contact portion 5d are bonded by ultrasonic bonding, the resin flow path 8 may be filled with the melt resin 6, and the filter element 2 and the container 3 may be caused to adhere to each other with the melt resin 6. As described above, to prevent the melt resin 6 injected into the inside of the resin flow path 8 from deforming the filter element 2 or entering the filter element 2, the filter element 2 is required to be sufficiently compressed by the gripper 9. Note that, in the case of ultrasonic bonding typically used for container adhesion, it is difficult to compress the filter element to have a high density. Even in the compressible case, leakage at a bonded portion of the bonded blood processing filter occurs, and a crack or the like occurs at the bonded portion due to excessive pressing of the containers against each other, which are problems in yield. On the contrary, in the case of the blood processing filter 1 according to this embodiment, this problem does not occur, which is advantageous.

EXAMPLES

The present invention will now be described in further detail below by way of examples. However, the present invention is not limited to these examples.

(Filtering Performance Evaluation on Whole Blood)

A whole blood preparation adjusted as follows was used for filtering performance evaluation. 2100 mL of pig whole blood was collected and mixed into a blood bag containing 320 mL of anticoagulant CPD, and relatively coarse aggregates generated during blood collection were removed by filtering with a preprocess filter other than the blood processing filters of Examples and Comparative Example, which will be described later. The preprocess filter has a configuration where twelve sheets with an average value of pore diameters of 60 μm and a weight per unit area of 50 g/m$^2$, eight sheets with an average value of pore diameters of 50 μm and a weight per unit area of g/m$^2$, and eight sheets with an average value of pore diameters of 50 μm and a weight per unit area of 30 g/m$^2$ are stacked from the upstream side in this order, and accommodated in a container made of rigid resin with a filtering area of 45 cm$^2$. The blood from which the coarse aggregates in blood collection had been removed by the preprocess filter was divided into 460 mL-portions and injected into respective bags on the day of blood collection. The thus obtained whole blood preparations were left at room temperature, and filtered with the filters of Examples and Comparative Example at room temperature on the day of blood collection. The filtering time from the start of filtering to the end was measured, and adopted as the filtering time. The leukocyte removing performance was calculated by the following Equation (1). It is demonstrated that the higher the value of the leukocyte removing performance is, the higher the performance of removing leukocytes is.

leukocyte removing performance=Log (concentration of leukocyte before filtering (cells/µL)/concentration of leukocyte after filtering (cells/µL)) (1)

The concentrations of leukocytes before and after filtering were measured using an automatic blood cell analyzer SF3000 (Sysmex Corporation).

Example 1

To create a blood processing filter of Example 1, the manufacturing method described in Description of Embodiment was used. That is, the inlet-side container element was formed by the one mold and the outlet-side container element was formed by the other mold, and subsequently the filter element was inserted into the outlet-side container element, and the inlet-side container element and outlet-side container element were joined with each other by moving the mold. Subsequently, the blood processing filter was created using the method of injecting the melt resin through the flow path of the mold formed at the periphery of the gripper of the inlet-side container element and the outlet-side container element into the resin flow path of the gripper and of causing the entire periphery of the gripper to adhere.

The container material and the melt resin injected into the resin flow path were polycarbonate resin, and the gap of the gripper, i.e., the distance between the surfaces of the inlet-side gripper and the outlet-side gripper that face with each other was 2.0 mm. The outer edge portion of the rear and front filtering surfaces of the filter element were configured such that the compression region clamped and compressed by the inlet-side gripper and the outlet-side gripper was a region having a distance range of 5 mm from the end surface of the filter element toward the inside. Furthermore, polyester nonwoven fabric was stacked according to the following configuration for use as the filter element. The original thickness of the filter element was 9 mm.
polyester nonwoven fabric 1 (the average fiber diameter is 12 µm, and the weight per unit area is 30 g/m$^2$) 6 sheets
polyester nonwoven fabric 2 (the average fiber diameter is 1.6 µm, and the weight per unit area is 66 g/m$^2$) 2 sheets
polyester nonwoven fabric 3 (the average fiber diameter is 1.2 µm, and the weight per unit area is 30 g/m$^2$) 32 sheets The result of an experiment through use of the thus created blood processing filter of Example 1 is shown in Table 1.

Example 2

A blood processing filter was created as with the Example 1 except that the container material and the melt resin injected into the resin flow path was a compound of styrene-butadiene block copolymer resin and polypropylene resin, and the gap of the gripper was 1.6 mm. The result of an experiment through use of this blood processing filter of Example 2 is shown in Table 1.

Example 3

A blood processing filter was created as with the Example 1 except that the container material was a compound of styrene-butadiene block copolymer resin and polypropylene resin, the melt resin injected into the resin flow path was polypropylene, and the gap of the gripper was 1.6 mm. The result of an experiment through use of this blood processing filter of Example 3 is shown in Table 1.

Comparative Example

An inlet-side container element was formed by one mold and an outlet-side container element was formed by the other mold, and subsequently the inlet-side container element and the outlet-side container element were taken out from the molds, and the filter element was inserted. The blood processing filter was created such that the inlet-side contact portion and the outlet-side contact portion were caused to adhere to each other, but the end surface of the filter element was not caused to adhere. The container material was a compound of styrene-butadiene block copolymer resin and polypropylene resin. The blood processing filter was created as with Example 1 except these points. The result of an experiment through use of this blood processing filter of this Comparative Example is shown in Table 1.

TABLE 1

| | Leukocyte Removing Performance (—) |
|---|---|
| Example 1 | 1.62 |
| Example 2 | 1.55 |
| Example 3 | 1.58 |
| Comparative Example | 0.32 |

According to the blood processing filters of Examples 1 to 3, sufficient leukocyte removing performances could be achieved. On the contrary, according to the blood processing filter of Comparative Example where the gripper was not caused to adhere to the end surface of the filter element with the melt resin, side leakage (side flow) where undesirable components flowed over the outer edge portion of the filter element without being filtered occurred. Thus, sufficient leukocyte removing performance cannot be achieved. In the blood processing filters of Example 1 to 3, since the gripper was caused to adhere to the filter element with the melt resin, the side leakage (side flow) could be prevented. In particular, in Example 1, the distance between the surfaces of the inlet-side gripper and the outlet-side gripper that face with each other (i.e., the compressibility ratio of the filter element at the gripper was the same) and the size of the compression region at the outer edge portion of the filter element were the same as those of the blood processing filter of Comparative Example. Consequently, it could be confirmed that even if the container element was made of a flexible material, the gripper was kept in the state of being caused to adhere to the end surface of the filter element with the melt resin and could thus prevent the side leakage (side flow) effectively, the compression region of the outer edge portion of the rear and front filtering surfaces of the filter element that was compressed by the gripper could be reduced, and the effective filtering area was facilitated to be widened in comparison with the case where the gripper was not caused to adhere to the end surface of the filter element with the melt resin.

REFERENCE SIGNS LIST

1 . . . Blood processing filter, 2 . . . Filter element, 2a, 2b . . . Filtering surface, 2c . . . End surface, 2d . . . Outer edge portion, 3 . . . Container, 3s . . . Internal space, 4 . . . Inlet-side container element, 4a . . . Outer surface, 4b . . . Inner surface, 4c . . . Inlet, 4d . . . Inlet-side contact portion, 4e . . . End surface, 4f . . . Inlet-side gripper, 4h . . . Rib, 4s . . . Inlet space, 5 . . . Outlet-side container element, 5a . . . Outer surface, 5b . . . inner surface, 5c . . . Outlet, 5d . . . Outlet-side contact portion, 5e . . . End surface, 5f . . . Outlet-side gripper, 5h . . . Rib, 5s . . . Outlet space, 6 . . . Melt resin, 7 . . . Contact portion, 8 . . . Resin flow path, 9 . . . Gripper, 12 . . . Movable die, 13 . . . Slidable die.

The invention claimed is:

1. A blood processing filter for removing undesirable components from liquid containing a blood component or blood, the filter comprising:
a sheet-shaped filter element; and
a container that includes an inlet-side container element and an outlet-side container element that are disposed to clamp the filter element, and has an internal space separated by the filter element into an inlet space and an outlet space,
wherein the filter element includes a filtering surface on a side of the inlet space, a filtering surface on a side of the outlet space, and an end surface along peripheries of the pair of filtering surfaces, and
the inlet-side container element and the outlet-side container element are provided with a gripper, and the gripper clamps and compresses an outer edge portion of the pair of filtering surfaces, and is caused to adhere to the end surface with melt resin,
at the gripper, the filter element is not melted, and
the same material as that of the container is adopted for the melt resin.

2. The blood processing filter according to claim 1, wherein the inlet-side container element and the outlet-side container element are made of flexible resin.

3. The blood processing filter according to claim 1, wherein the gripper further includes a resin flow path that surrounds the end surface of the filter element and is provided with the melt resin.

4. The blood processing filter according to claim 3, wherein the inlet-side container element, the outlet-side container element, and the filter element adhere over an entire periphery of the gripper by the resin flow path being filled with the melt resin.

5. A method of manufacturing a blood processing filter for removing undesirable components from liquid containing a blood component or blood, the method comprising:

injection-molding an inlet-side container element using one mold, and an outlet-side container element using another mold;
inserting a filter element into the inlet-side container element or the outlet-side container element;
mold-fitting the molds, and joining the inlet-side container element and the outlet-side container element to each other; and
causing the inlet-side container element and the outlet-side container element to adhere to each other with melt resin,
wherein the filter element includes a filtering surface on a side of an inlet space, a filtering surface on a side of an outlet space, and an end surface along peripheries of the pair of filtering surfaces,
the inlet-side container element and the outlet-side container element are provided with a gripper, and the gripper clamps and compresses an outer edge portion of the pair of filtering surfaces, and is caused to adhere to the end surface with melt resin,
at the gripper, the filter element is not melted, and
adopting the same material as that of the container for the melt resin.

6. The blood processing filter according to claim 1, wherein an outer edge portion of the gripper is configured to grip the melt resin, and an inner portion of the gripper is configured to clamp the outer edge portion of the pair of filtering surfaces.

7. The blood processing filter according to claim 6, wherein the outer edge portion is configured to filter blood.

8. A blood processing filter comprising:
a sheet-shaped filter element; and
a container that includes an inlet-side container element and an outlet-side container element that are disposed to clamp the filter element, and has an internal space separated by the filter element into an inlet space and an outlet space,
wherein the filter element includes a filtering surface on a side of the inlet space, a filtering surface on a side of the outlet space, and an end surface along peripheries of the pair of filtering surfaces,
the inlet-side container element and the outlet-side container element are provided with a gripper, and the gripper clamps and compresses a non-melted outer edge portion of the filter element, and
the same material as that of the container is adopted for the melt resin.

9. The blood processing filter according to claim 8, wherein a first portion of the gripper is configured to grip the melt resin, and a second portion of the gripper is configured to clamp the non-melted outer edge portion of the pair of filtering surfaces.

10. The blood processing filter according to claim 9, wherein the non-melted outer edge portion is configured to filter blood.

* * * * *